US010605630B2

(12) United States Patent
Lee et al.

(10) Patent No.: US 10,605,630 B2
(45) Date of Patent: Mar. 31, 2020

(54) TACTILE SENSOR, METHOD FOR MANUFACTURING THE SAME, THREE-DIMENSIONAL MAPPING METHOD

(71) Applicant: ULSAN NATIONAL INSTITUTE OF SCIENCE AND TECHNOLOGY (UNIST), Ulsan (KR)

(72) Inventors: Jiseok Lee, Ulsan (KR); Hyunhyub Ko, Ulsan (KR); Seonghyeon Ahn, Ulsan (KR)

(73) Assignee: Ulsan National Institute of Science and Technology (UNIST), Ulasn (KR)

( * ) Notice: Subject to any disclaimer, the term of this patent is extended or adjusted under 35 U.S.C. 154(b) by 186 days.

(21) Appl. No.: 15/996,262

(22) Filed: Jun. 1, 2018

(65) Prior Publication Data

US 2019/0056246 A1    Feb. 21, 2019

(30) Foreign Application Priority Data

Aug. 21, 2017   (KR) .......................... 10-2017-0105419

(51) Int. Cl.
*G01D 5/30* (2006.01)
*A61B 5/1172* (2016.01)
*G06K 9/00* (2006.01)

(52) U.S. Cl.
CPC .............. *G01D 5/30* (2013.01); *A61B 5/1172* (2013.01); *G06K 9/0004* (2013.01); *A61B 2562/0247* (2013.01)

(58) Field of Classification Search
CPC ....... G01D 5/30; A61B 5/1172; G06K 9/0004
See application file for complete search history.

(56) References Cited

U.S. PATENT DOCUMENTS

| 2011/0058091 | A1* | 3/2011 | Hsu ....................... A61B 5/1172 348/340 |
| 2012/0062364 | A1* | 3/2012 | Rowe ................... G06K 9/0004 340/5.82 |
| 2012/0318074 | A1* | 12/2012 | Kyung .................... G01L 1/243 73/862.624 |
| 2017/0254996 | A1 | 9/2017 | Lee et al. |
| 2019/0125221 | A1* | 5/2019 | Kobayashi ........... G02B 6/0023 |

FOREIGN PATENT DOCUMENTS

| JP | 2013-105627 A | 5/2013 |
| JP | 2014-135400 A | 7/2014 |
| KR | 2012-0139264 A | 12/2012 |
| KR | 2016-0129470 A | 11/2016 |

(Continued)

OTHER PUBLICATIONS

Eric V. Eason et al., *Stress Distribution and Contact Area Measurements of a Gecko Toe Using a High-Resolution Tactile Sensor*, Bioinspiration & Biomimetics, vol. 10, 2015, 17 pp.

(Continued)

*Primary Examiner* — Edwin C Gunberg
(74) *Attorney, Agent, or Firm* — Workman Nydegger

(57) ABSTRACT

Provided are a tactile sensor, a method of manufacturing the tactile sensor, and a three-dimensional (3D) mapping method. The tactile sensor includes a total reflection layer; a pixel layer formed on the total reflection layer and including a microarray; and a tactile pad layer formed on the pixel layer.

18 Claims, 7 Drawing Sheets

(56) References Cited

FOREIGN PATENT DOCUMENTS

| KR | 1020160129470 A | 11/2016 |
| KR | 10-1754146 A | 7/2017 |

OTHER PUBLICATIONS

Jiao Chen et al., *Upconversion Nanomaterials: Synthesis, Mechanism, and Applications in Sensors*, Sensors, vol. 12, 2012, pp. 2414-2435.

Fan Zhang et al., *Uniform Nanostructured Arrays of Sodium Rare-Earth Fluorides for Highly Efficient Multicolor Upconversion Luminescense*, Angewandte Chemie, vol. 119, 2007, pp. 8122-8125.

Shuwei Hao et al., *Sensing Using Rare-Earth-Doped Upconversion Nano-Particles*, Theranostics 2013, vol. 3, Issue 5, pp. 331-345.

Danny Vennerberg et al., *Upconversion Nanocrystals Synthesis, Properties, Assembly and Applications*, Science of Advanced Materials, vol. 3, 2011, pp. 26-40.

\* cited by examiner (a)  (b)  (c)

TACTILE SENSOR, METHOD FOR MANUFACTURING THE SAME, THREE-DIMENSIONAL MAPPING METHOD

CROSS-REFERENCE TO RELATED APPLICATION(S)

This application claims the priority benefit of Korean Patent Application No. 10-2017-0105419 filed on Aug. 21, 2017, in the Korean Intellectual Property Office, the disclosure of which is incorporated herein by reference for all purposes.

BACKGROUND

1. Field

At least one example embodiment relates to a tactile sensor, a method of manufacturing the tactile sensor, and a three-dimensional (3D) mapping method.

2. Related Art

In general, a tactile sensor refers to a biomimetic sensor capable of sensing information about a surrounding environment through contact, such as a contact force, a vibration, surface roughness, and a temperature change with respect to a thermal conductivity. The tactile sensor capable of replacing a tactile sense may be used for various types of medical diagnoses and procedures, such as a cancer diagnosis and a microsurgery in the blood vessels and may be applied to a tactile presentation technology that is important in future virtual environment implementation technology.

The tactile sensor includes a transducer that converts a physical quantity, such as a force and a temperature, to an electrical signal, and a detection circuit that receives and detects the electrical signal generated by the transducer and outputs the detected electrical signal to an output. A conversion scheme may include a strain gauge scheme, a piezoresistive scheme, a capacitive scheme, a conductive rubber ink scheme, a piezoelectric scheme, and an optical scheme. Here, an optical tactile sensor senses only a two-dimensional (2D) tactile sense and thus, may not accurately recognize forces in various directions, such as a vertical direction, a horizontal direction, and the like. In addition, the optical tactile sensor has a relatively narrow color change range, requires a relatively large physical transformation, has a slow response speed and recovery speed, and is vulnerable to an external environment.

BRIEF SUMMARY

At least one example embodiment provides a tactile sensor having a high sensitivity, a multi-functionality, and a multi-directionality by recognizing a direction and a magnitude of an external stimulus, a method of manufacturing the tactile sensor, and a three-dimensional (3D) mapping method.

However, the objects to be solved by the present disclosure are not limited thereto and other objects not described herein may be explicitly understood by one of ordinary skill in the art from the following description.

According to an aspect of at least one example embodiment, there is provided a tactile sensor including a total reflection layer; a pixel layer formed on the total reflection layer and including a microarray; and a tactile pad layer formed on the pixel layer.

The microarray may include at least one color includes at least one color conversion mediator selected from among a upconverting nanocrystal (UCN) particle, a quantum dot, and a fluorescence dye.

The UCN particle may include at least one of (NaYF4:Yb3+,Er3+), (NaYF4:Yb3+,Tm3+), (NaGdF4:Yb3+,Er3+), (NaYF4:Yb3+,Er3+/NaGdF4), and (NaGdF4:Yb3+,Er3+/NaGdF4).

The quantum dot may include at least one of a group II-VI compound, a group III-V compound, a group IV-VI compound, a group IV element, and a group IV compound.

The fluorescence dye may include at least one inorganic material selected from CdSe, CdSe/ZnS, CdTe/CdS, CdTe/CdTe, ZnSe/ZnS, ZnTe/ZnSe, PbSe, PbS InAs, InP, InGaP, InGaP/ZnS, and HgTe; and at least one organic material selected from Cy3.5, Cy5, Cy5.5, Cy7, indocyanine green (ICG), cypate, ITCC, NIR820, NIR2, IRDye78, IRDye80, IRDye82, oxazines-based cresy violet, nile blue, oxazine 750, and rhodamines-based rhodamine800 and texas red.

At least one light selected from among near infrared (NIR) light, visible light, and ultraviolet (UV) light may be irradiated toward the total reflection layer.

The microarray may be configured by arranging a plurality of structures at predetermined intervals.

Each of the plurality of structures may be provided in a shape of at least one of a dome, a cylinder, a cone, a ridge, a faceted cone, a faceted cylinder, a faceted semi-sphere, and a faceted sphere.

Each of the plurality of structures may have a diameter of 10 μm to 100 μm and a height of 5 μm to 50 μm.

The microarray may include the plurality of structures each having a different height and a different shape per single pixel.

The tactile sensor may further include a spacer layer provided between the total reflection layer and the pixel layer.

A refractive index of the total reflection layer is greater than that of the spacer layer.

According to another aspect of at least one example embodiment, there is provided a method of manufacturing a tactile sensor, the method including preparing a total reflection layer using an acrylic material; forming a pixel layer that includes a microarray on which a plurality of structures is arranged at predetermined intervals and a tactile pad layer that includes a microarray on which a plurality of structures is arranged to interlock with the plurality of structures included in the pixel layer; providing the pixel layer on the total reflection layer; and providing the tactile pad layer on the pixel layer.

The preparing of the total reflection layer may include preparing the total reflection layer by replacing the acrylic material with halogen and by adding a metal oxide nano particle to the acrylic material replaced with the halogen.

The tactile sensor manufacturing method may further include preparing a porous spacer layer after the preparing of the total reflection layer.

The pixel layer may form the microarray including the plurality of structures using a 3D optical etching method after dispersing at least one color conversion mediator selected from among an UCN particle, a quantum dot, and a fluorescence dye to flexible resin.

The tactile pad layer may form the microarray on which the plurality of structures is arranged to interlock with the plurality of structures included in the pixel layer using an elastic composite material.

According to another aspect of at least one example embodiment, there is provided a 3D mapping method including acquiring a 3D image based on color information provided in response to a tactile signal sensed by a tactile sensor.

A tactile sensor according to some example embodiments is configured to recognize a direction and a magnitude of an external stimulus and may have various directivities such as a very minute pressure in a vertical direction, a horizontal direction, and the like, a shear force, a tensile force, a twist, and a bend, and may distinguish each force through each different signal pattern. Also, the tactile sensor may have a fast reaction speed to a change in the pressure, may realize a high durability and resilience, and may perform an accurate sensing operation. Also, since the tactile sensor may sense a tactile sense in real time, power for sensing an electrical signal is not required. Accordingly, the tactile sensor may be applicable as a next-generation material to the low-power sensor device market.

A method of manufacturing a tactile sensor according to some example embodiments may provide a tactile sensor with a high sensitivity, a multi-functionality, and a multi-directionality capable of sensing various external forces by manufacturing the tactile sensor in a microarray interlocking structure.

A 3D mapping method according to some example embodiments may be applied to a biometric security technology such as a fingerprint recognition, a medical device for rehabilitation training and physical therapy, and the like.

Additional aspects of example embodiments will be set forth in part in the description which follows and, in part, will be apparent from the description, or may be learned by practice of the disclosure.

DETAILED DESCRIPTION

Figure 1:
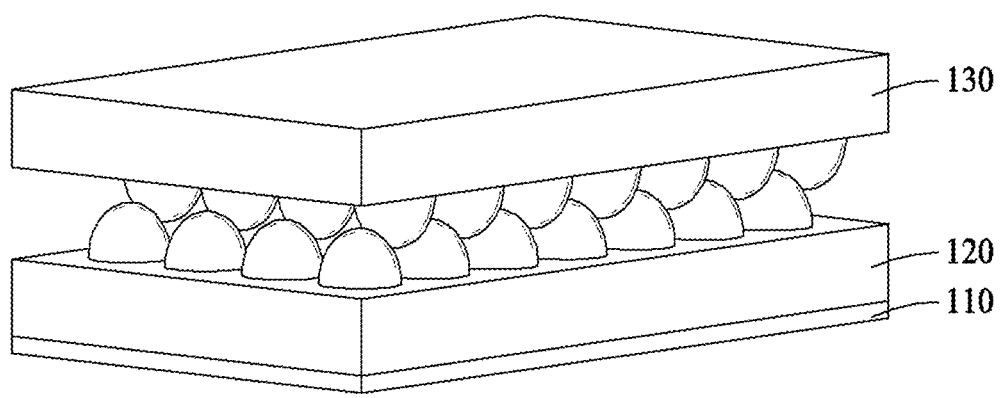
FIG. 1 is a perspective view of a tactile sensor according to an example embodiment.

Hereinafter, some example embodiments will be described in detail with reference to the accompanying drawings. In the description of example embodiments, detailed description of well-known related structures or functions will be omitted when it is deemed that such description will cause ambiguous interpretation of the present disclosure. Also, terminologies used herein are defined to appropriately describe the example embodiments and thus, may be changed depending on a user, the intent of an operator, or a custom. Accordingly, the terms must be defined based on the following overall description of this specification. Regarding the reference numerals assigned to the elements in the drawings, it should be noted that the same elements will be designated by the same reference numerals, wherever possible, even though they are shown in different drawings.

Terms, such as first, second, and the like, may be used herein to describe components. Each of these terminologies is used merely to distinguish a corresponding component from other component(s). For example, a first component may be referred to as a second component, and similarly the second component may also be referred to as the first component.

It should be noted that if it is described that one component is "connected", "coupled", or "joined" to another component, a third component may be present between the component and the other component although the component may be directly connected, coupled, or joined to the other component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Hereinafter, a tactile sensor, a method of manufacturing the tactile sensor, and a three-dimensional (3D) mapping method according to example embodiments will be described with reference to the accompanying drawings. However, they are provided as examples only and the present disclosure is not limited thereto or restricted thereby.

According to an example embodiment, there is provided a tactile sensor including a total reflection layer, a pixel layer formed on the total reflection layer and including a microarray, and a tactile pad layer formed on the pixel layer.

Figure 2:
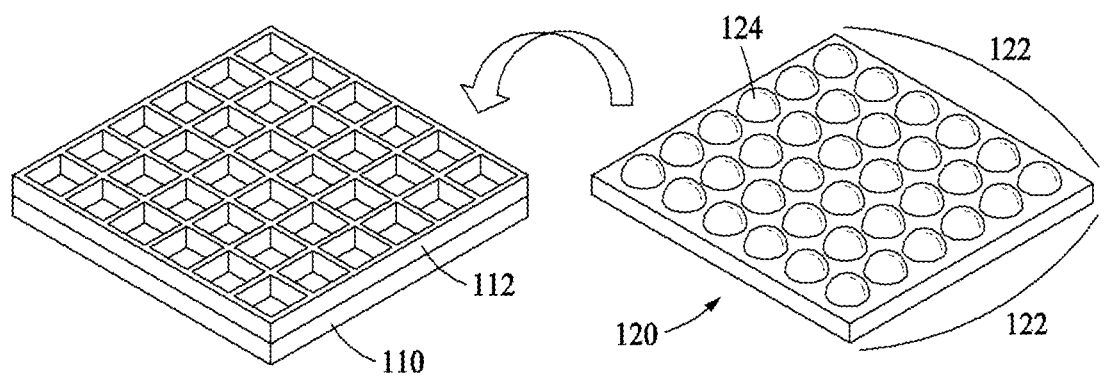
FIG. 2 is a perspective view of a total reflection layer, a spacer layer, and a pixel layer included in a tactile sensor according to an example embodiment.

FIG. 1 is a perspective view of a tactile sensor according to an example embodiment, and FIG. 2 is a perspective view of a total reflection layer, a spacer layer, and a pixel layer included in a tactile sensor according to an example embodiment. Referring to FIGS. 1 and 2, a tactile sensor 100 includes a total reflection layer 110, a spacer layer 112, a pixel layer 120, and a tactile pad layer 130.

According to an aspect, the total reflection layer 110 may totally reflect light that passes through the total reflection layer 110.

At least one of near infrared (NIR) light, visible light, and ultraviolet (UV) light may be irradiated toward the total reflection layer 110. A color conversion mediator may exhibit various colors by the total reflection of the NIR light, the visible light, and the UV light. For example, light with an NIR wavelength may be used and a laser with a NIR wavelength of 900 nm and 1000 nm may be employed for the NIR wavelength. For example, a laser with a wavelength of 980 nm may be used, for example, in terms of absorbing upconverting nanocrystal (UCN) particles.

A refractive index of the total reflection layer 110 may be greater than that of the spacer layer 112. To enable the efficient total reflection of the total reflection layer 110, a difference between the refractive index of the spacer layer 112 and the refractive index of the total reflection layer 110 needs to be great. To increase the difference in the refractive index, a relatively high refractive index may be acquired by adding metal oxide-based nanoparticles to the total reflection layer 110.

The pixel layer 120 may include a microarray 124 on which a plurality of structures 122 is arranged at predetermined intervals. The structure 122 may sense a pressure applied by the tactile pad layer 130.

The structure 122 may be maintained by way of the porous spacer layer 112 provided between the total reflection layer 110 and the pixel layer 120.

The tactile pad layer 130 may be provided in an interlocking structure to be capable of interlocking with the plurality of structures 122 formed on the pixel layer 120. Due to the interlocking structure of the tactile pad layer 130, stress may be concentrated locally relative to a multi-directional force. Accordingly, compared to a tactile pad layer in a planar structure according to the related art, it is possible to manufacture a high resolution tactile pad layer and to sense a multi-directional tactile sense based on a difference in a contact area.

The microarray 124 of the pixel layer 120 may be formed of a flexible material and may be in contact with the total reflection layer 110 in response to a pressure applied to the tactile pad layer 130. Here, various combinations of colors may be exhibited by a color conversion mediator (not shown) included in the microarray 124 based on a direction and magnitude of the applied pressure.

The microarray 124 may include at least one color conversion mediator selected from among a UCN particle, a quantum dot, and a fluorescence dye.

According to an aspect, UCN particles may be prepared from a large number of types of nanocrystalline groups. In general, the UCN particles may include three sensitizers, an emitter, and a host matrix. The sensitizers may include $Yb^{3+}$ and may also include $Nd^{3+}$ ions. The emitter generally includes $Tm^{3+}$, $Er^{3+}$, and $Ho^{3+}$. The host matrix is represented as $AReF_4$ and includes Li/k in addition to A=Na. Here, Re includes Y/Lu/Gd. The UCN particles may include various combinations of lanthanide ions.

The UCN particle may include at least one of ($NaYF_4$:$Yb^{3+}$,$Er^{3+}$), ($NaYF_4$:$Yb^{3+}$,$Tm^{3+}$), ($NaGdF_4$:$Yb^{3+}$,$Er^{3+}$), ($NaYF_4$:$Yb^{3+}$,$Er^{3+}$/$NaGdF_4$), and ($NaGdF_4$:$Yb^{3+}$,$Er^{3+}$/$NaGdF_4$). However, it is provided as an example only. A mixture of phospholipid-PEG and phospholipid-PEG-amine, $SiO_2$, and fluorine may be coated on the surface, and oxidation and acrylation may be applied on the surface so that such UCN particles may be uniformly distributed on photo polymerization resin.

The UCN particles may absorb NIR photons through an optical upconversion process and emit visible photons or near-UV photons. For example, ($NaYF_4$:$Yb^{3+}$,$Er^{3+}$) nanocrystals may be most frequently used in the study on UCN particles, and may absorb photons with a wavelength of 980 nm and emit photons of a visible area. The UCN particles may be excited by biocompatible NIR light and emit light in a visible area and thus, may hardly damage, for example, a body cell sample to be used for fingerprint recognition, may prevent self-emission, may significantly increase bio-transmittance, and may acquire an image through a general charged coupled device (CCD) for not separate NIR but visible light. Also, the UCN particles may acquire consecutive long-hour optical images due to an absence of photoblinking or photobleaching. Since the UCN particle correspond to a multi-purpose nanomaterial capable of performing various biological functions through the surface modification, a universal and general biological application is enabled.

The quantum dot may include at least one of a group II-VI compound, a group III-V compound, a group IV-VI compound, a group IV element, and a group IV compound.

According to an aspect, the II-VI compound may be selected from among at least one binary compound selected from among CdSe, CdTe, ZnS, ZnSe, ZnTe, ZnO, HgS, HgSe, HgTe, MgSe, and MgS; at least one ternary compound selected from among CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and MgZnS; and at least one quaternary compound selected from among HgZnTeS, CdZnSeS, CdZnSeTe, CdZnSTe, CdHgSeS, CdHgSeTe, CdHgSTe, HgZnSeS, HgZnSeTe, and HgZnSTe.

According to an aspect, the group III-V compound may be selected from among at least one binary compound selected from among GaN, GaP, GaAs, GaSb, AlN, AlP, AlAs, AlSb, InN, InP, InAs, and InSb; at least one ternary compound selected from among GaNP, GaNAs, GaNSb, GaPAs, GaPSb, AlNP, AlNAs, AlNSb, AlPAs, AlPSb, InNP, InNAs, InNSb, InPAs, InPSb, and GaAlNP; and at least one quaternary compound selected from among GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, and InAlPSb.

According to an aspect, the group IV-VI compound may be selected from at least one binary compound selected from among SnS, SnSe, SnTe, PbS, PbSe, and PbTe; at least one ternary compound selected from among SnSeS, SnSeTe, SnSTe, PbSeS, PbSeTe, PbSTe, SnPbS, SnPbSe, and SnPbTe; and at least one quaternary compound selected from among SnPbSSe, SnPbSeTe, and SnPbSTe.

According to an aspect, the group IV element may be selected from among Si, Ge, and a mixture thereof. The group IV compound may be a binary compound selected from among SiC, SiGe, and a mixture thereof.

The quantum dot may be one in which a binary compound, a ternary compound, or a quaternary compound is present within a particle at uniform concentration, or is dividedly distributed at partially different concentration within the same particle. Also, a single quantum dot may have a core/shell structure that surrounds another quantum dot. An interface between a core and a shell may have a concentration gradient in which a concentration of an element present in the shell decreases with getting closer to a center.

For example, the quantum dot may have a full width at half maximum (FWHM) of a spectrum with an emission wavelength of 45 nm or less. In this range, color purity or color reproducibility may be enhanced. Further, since light emitted from the quantum dot may be emitted in every direction, a wide viewing angle may be enhanced. The quantum dot may include at least one of a nanoparticle, a nanotube, a nanowire, and a nanofiber, and a planar nanoparticle in a spherical shape, a pyramidal shape, a multi-arm shape, or a cubic shape.

The fluorescence dye may include at least one organic material selected from among CdSe, CdSe/ZnS, CdTe/CdS, CdTe/CdTe, ZnSe/ZnS, ZnTe/ZnSe, PbSe, PbS InAs, InP, InGaP, InGaP/ZnS, and HgTe; and at least one organic material selected from among Cy3.5, Cy5, Cy5.5, Cy7, indocyanine green (ICG), cypate, ITCC, NIR820, NIR2, IRDye78, IRDye80, IRDye82, oxazines-based cresy violet, nile blue, oxazine 750, and rhodamines-based rhodamine800 and texas red.

According to an aspect, the microarray 122 may include various colors and, if necessary, may include a preset number of colors. For example, the microarray 122 may include one to five colors per pixel. The five colors may include, for example, yellow, cyan, blue, purple, and red. Also, the five colors may include yellow, red, green, blue, and white.

Figure 3A:
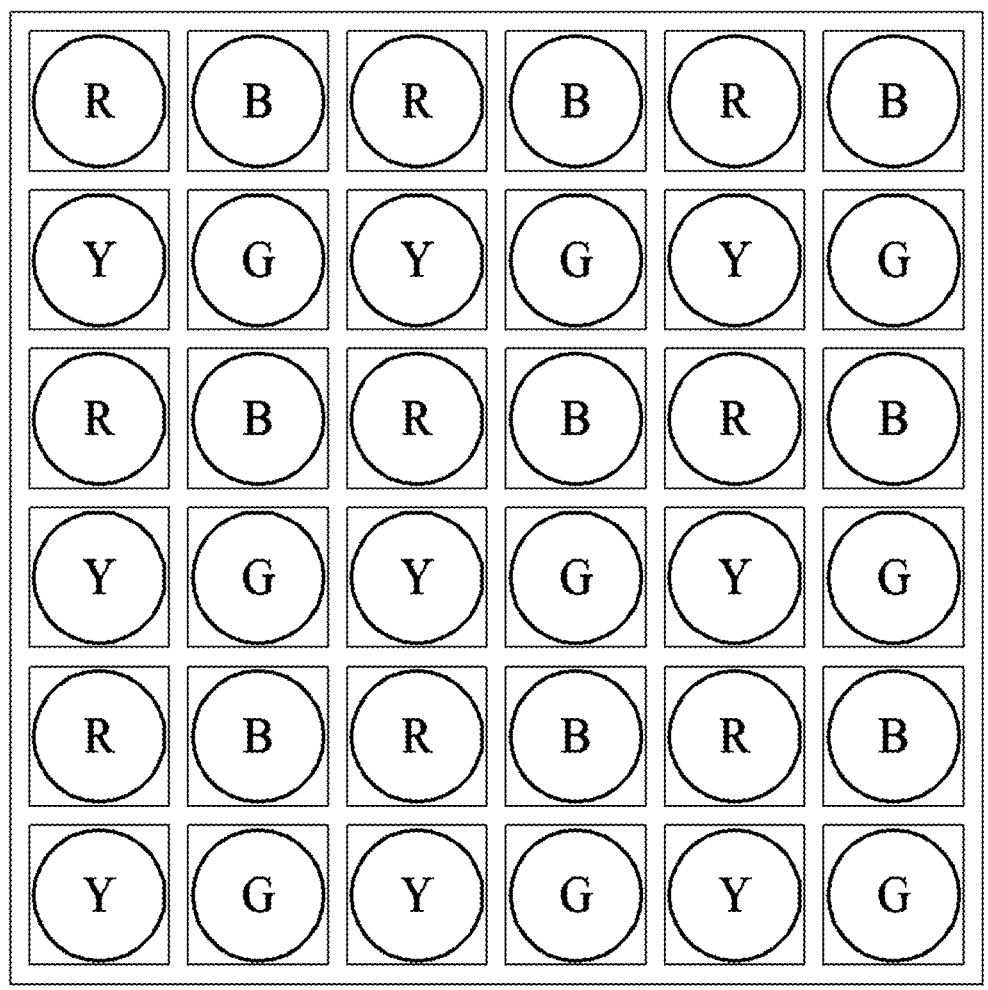
FIGS. 3A and 3B illustrate examples of a microarray based on a color of a pixel layer according to an example embodiment.
Figure 3B:
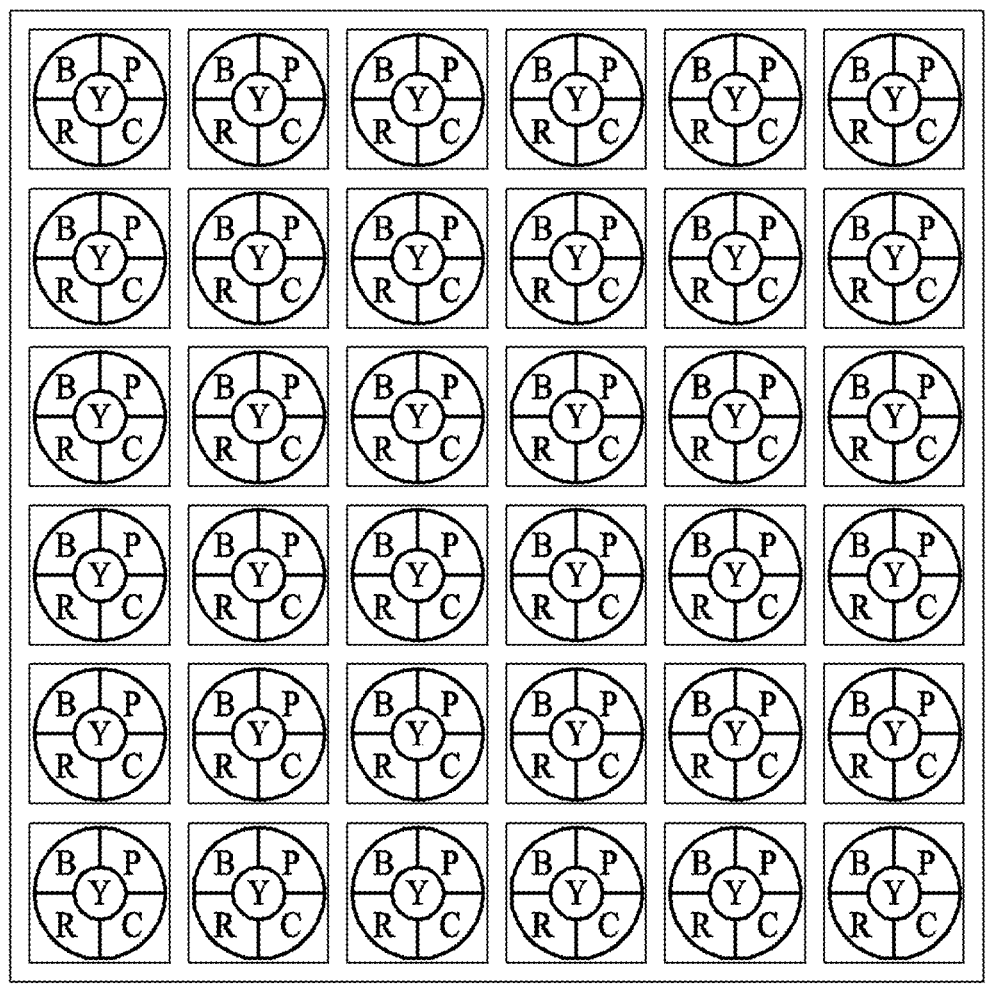

FIGS. 3A and 3B illustrate examples of a microarray based on a color of a pixel layer according to an example embodiment. Referring to FIG. 3A, the microarray may include a single color per pixel. For example, a single color, each of yellow (Y), red (R), green (G), and blue (B), may be included in each single pixel. Referring to FIG. 3B, the microarray may include five colors per pixel. For example, all of the five colors, yellow (Y), cyan (C), blue (B), purple (P), and red (R), may be included in each pixel.

According to an aspect, the structure 124 may be provided in a shape of at least one of a dome, a cylinder, a cone, a ridge, a faceted cone, a faceted cylinder, a faceted semisphere, and a faceted sphere.

Figure 4A:
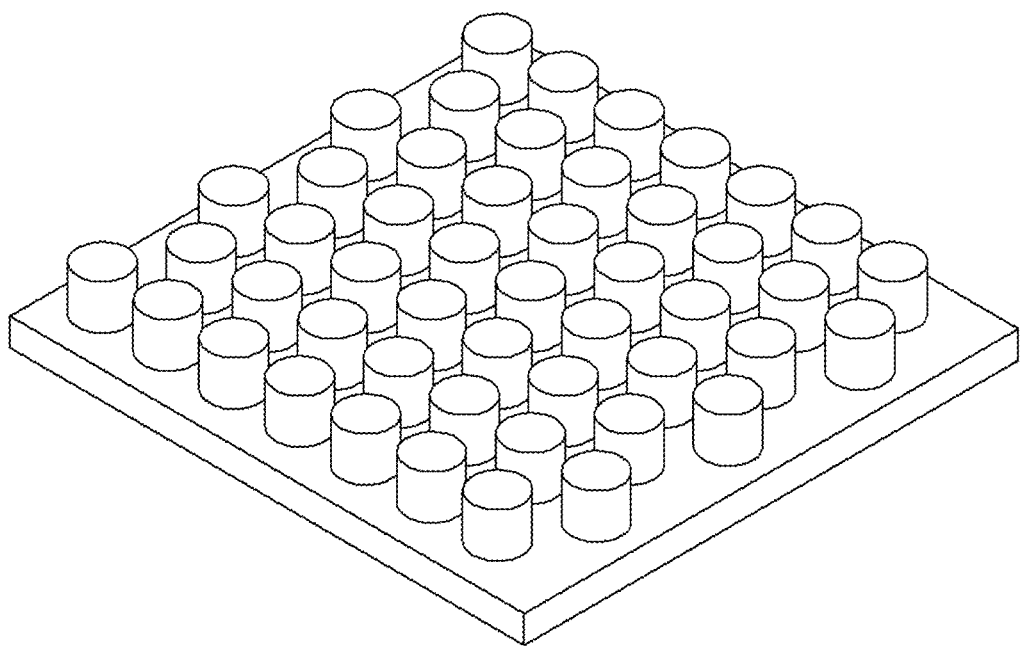
FIGS. 4A and 4B illustrate examples of a shape of a structure of a microarray according to an example embodiment.
Figure 4B:
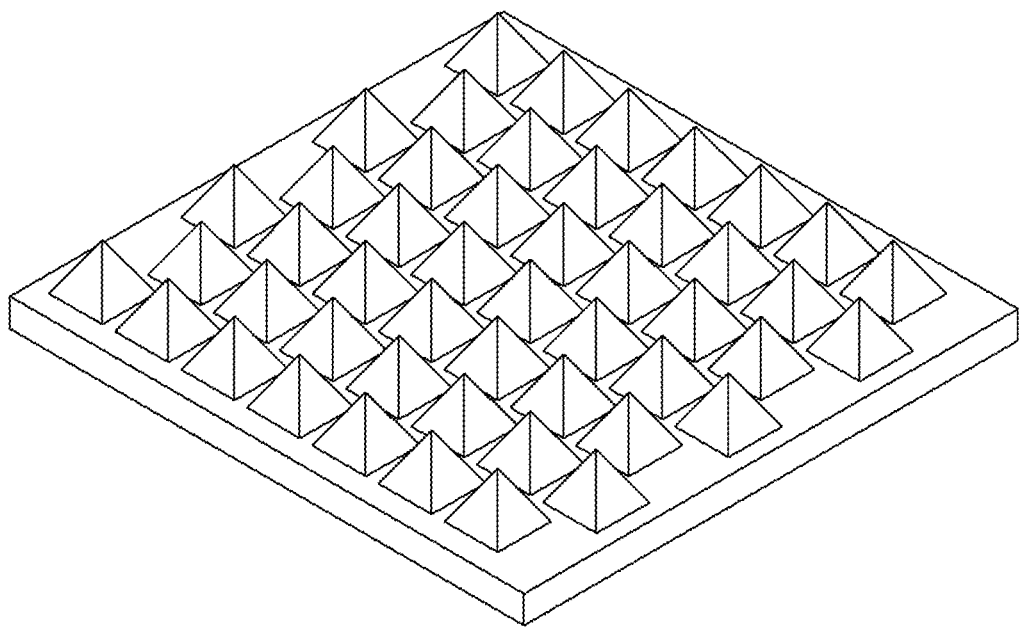

FIGS. 4A and 4B illustrate examples of a shape of a structure of a microarray according to an example embodiment. The shape of the structure of the microarray according to the example embodiment may be provided in a shape of a dome as shown in FIGS. 1 and 2. However, it is provided as an example only. The structure of the microarray may be provided in a shape of a cylinder of FIG. 4A, may be provided in a shape of a square pyramid of FIG. 4B, and may be provided in any shape as described above.

According to an aspect, the structure 124 may have a diameter of 10 μm to 100 μm and a height of 5 μm to 50 μm. However, it is provided as an example only. Accordingly, the diameter and/or the height of the structure 124 may be adjusted. The diameter and/or the height of the structure 124 needs to be appropriately configured to cause a change in a contact area by the interlocking tactile pad layer 130. If the structure 124 is set to have a significantly great height, the structure 124 may be easily deformed or fragile.

The microarray 122 may include the plurality of structures 124 each having a different height and a different shape per pixel. By adjusting a height and a shape of the structure 124 to be different for each pixel, the pixel layer 120 may be pressed as a magnitude of pressure applied to the structure 124 increases. In this state, remaining pixels may sequentially make a contact with the total reflection layer 110 and colors may be sequentially exhibited. By adjusting the height and the shape of the structure 124 to be different for each pixel, a very minute pressure may be sensed in a vertical direction, a horizontal direction, and the like.

According to example embodiments, a size of a structure, a number of colors per pixel, and a pattern of a microarray may be variously adjusted based on a purpose of a tactile sensor.

A tactile sensor according to some example embodiments is configured to recognize a direction and a magnitude of an external stimulus and thus may have various directivities such as a very minute pressure in a vertical direction, a horizontal direction, and the like, a shear force, a tensile force, a twist, and a bend, and may distinguish each force through each different signal pattern. Also, the tactile sensor may have a fast reaction speed to a change in the pressure, may realize a high durability and resilience, and may perform an accurate sensing operation. Also, since the tactile sensor may sense a tactile sense in real time, power for sensing an electrical signal is not required. Accordingly, the tactile sensor may be applicable as a next-generation material to the low-power sensor device market.

According to another example embodiment, there is provided a method of manufacturing a tactile sensor, the method including preparing a total reflection layer using an acrylic material; forming a pixel layer that includes a microarray on which a plurality of structures is arranged at predetermined intervals and a tactile pad layer that includes a microarray on which a plurality of structures is arranged to interlock with the plurality of structures included in the pixel layer; providing the pixel layer on the total reflection layer; and providing the tactile pad layer on the pixel layer.

Figure 5:
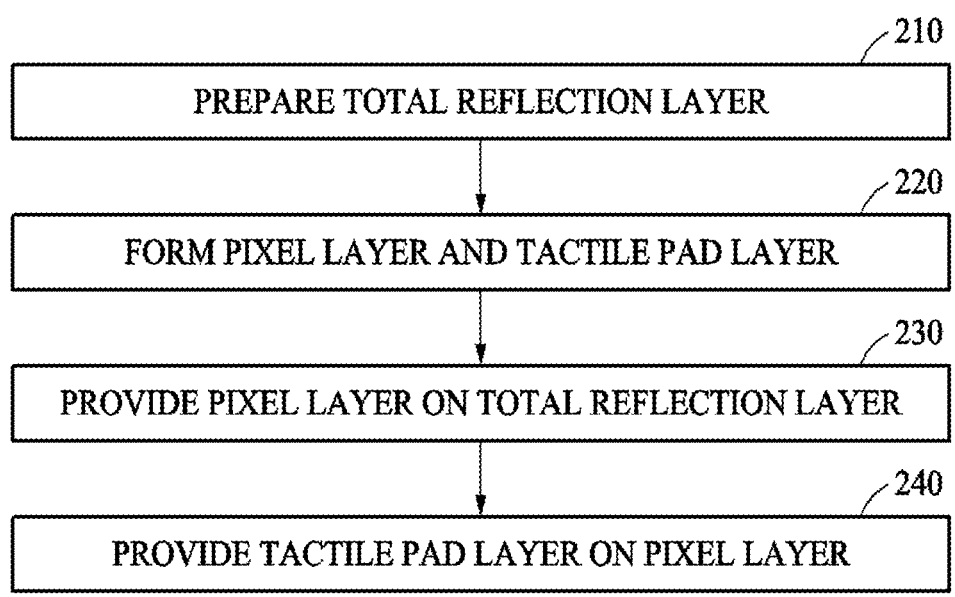
FIG. 5 is a flowchart illustrating a method of manufacturing a tactile sensor according to an example embodiment.

FIG. 5 is a flowchart illustrating a method of manufacturing a tactile sensor according to an example embodiment. Referring to FIG. 5, the tactile sensor manufacturing method may include operation 210 of preparing a total reflection layer, operation 220 of forming a pixel layer and a tactile pad layer, operation 230 of providing the pixel layer on the total reflection layer, and operation 240 of providing the tactile pad layer on the pixel layer.

According to an aspect, operation 210 may include preparing the total reflection layer by replacing the acrylic material with halogen and by adding a metal oxide nano particle to the acrylic material replaced with the halogen.

The acrylic material may include, for example, at least one of polyurethane acrylate, epoxy acrylate, urethane acrylate, melamine acrylate, silicone acrylate, phenoxy resin, and halogenated urethane acrylate.

The metal oxide nanoparticle may include, for example, at least one of zirconium oxide ($ZrO_2$), titanium oxide ($TiO_2$), silicon oxide ($SiO_2$), indium titanium oxide (ITO), tin oxide ($SnO_2$), indium oxide ($In_2O_3$) and antimony titanium oxide (ATO).

The tactile sensor manufacturing method may further include preparing a porous spacer layer after performing operation 210.

The structure of the microarray may be maintained by way of the porous space layer. The porous spacer layer may be prepared to have a relatively low refractive index by adjusting a size and concentration of a polystyrene particle and a photocuring level of polydimethylsiloxane.

According to an aspect, a difference between a refractive index of the spacer layer and a refractive index of the total reflection layer needs to be great to enable the effective total refection of the total reflection layer. A relatively high refractive index may be acquired by adding metal oxide nanoparticles to the total reflection layer. A refractive index of the acrylic material replaced with halogen may be 1.3 to 1.6 and, when the metal oxide nano particle is added, the refractive index may be 1.7 to 1.8.

In operation 220, each of the pixel layer and the tactile pad layer may be formed.

According to an aspect, the pixel layer may form the microarray including a plurality of structures using a 3D optical etching method after stably distributing at least one color conversion mediator selected from among a UCN particle, a quantum dot, and a fluorescence dye to flexible resin. The flexible resin may be used to provide flexibility that enables the tactile sensor to be flexibly twisted or bendable. To increase the distributivity relative to the flexible resin, surface modification may be applied to at least one color conversion mediator selected from the UCN particle, the quantum dot, and the fluorescence dye.

According to an aspect, UCN particles may be prepared from a large number of types of nanocrystalline groups. In general, the UCN particles may include three sensitizers, an emitter, and a host matrix. The sensitizers may include $Yb^{3+}$ and may also include $Nd^{3+}$ ions. The emitter generally includes $Tm^{3+}$, $Er^{3+}$, and $Ho^{3+}$. The host matrix is represented as $AReF_4$ and includes Li/k in addition to A=Na. Here, Re includes Y/Lu/Gd. The UCN particles may include various combinations of lanthanide ions.

The UCN particle may include at least one of (NaYF4: Yb3+,Er3+), (NaYF4:Yb3+,Tm3+), (NaGdF4:Yb3+,Er3+), (NaYF4:Yb3+,Er3+/NaGdF4), and (NaGdF4:Yb3+,Er3+/ NaGdF4). However, it is provided as an example only. A mixture of phospholipid-PEG and phospholipid-PEG-amine, SiO2, and fluorine may be coated on the surface, and oxidation and acrylation may be applied on the surface so that such UCN particles may be uniformly distributed on photo polymerized resin.

The quantum dot may include at least one of a group II-VI compound, a group III-V compound, a group IV-VI compound, a group IV element, and a group IV compound.

According to an aspect, the group II-VI compound may be selected from among at least one binary compound selected from among CdSe, CdTe, ZnS, ZnSe, ZnTe, ZnO, HgS, HgSe, HgTe, MgSe, and MgS; at least one ternary compound selected from among CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, and MgZnS; and at least one quaternary compound selected from among HgZnTeS, CdZnSeS, CdZnSeTe, CdZnSTe, CdHgSeS, CdHgSeTe, CdHgSTe, HgZnSeS, HgZnSeTe, and HgZnSTe.

According to an aspect, the group III-V compound may be selected from among at least one binary compound selected from among GaN, GaP, GaAs, GaSb, AlN, AlP, AlAs, AlSb, InN, InP, InAs, and InSb; at least one ternary compound selected from among GaNP, GaNAs, GaNSb, GaPAs, GaPSb, AlNP, AlNAs, AlNSb, AlPAs, AlPSb, InNP, InNAs, InNSb, InPAs, InPSb, and GaAlNP; and at least one quaternary compound selected from among GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, and InAlPSb.

According to an aspect, the group IV-VI compound may be selected from among at least one binary compound selected from among SnS, SnSe, SnTe, PbS, PbSe, and PbTe; at least one ternary compound selected from among SnSeS, SnSeTe, SnSTe, PbSeS, PbSeTe, PbSTe, SnPbS, SnPbSe, and SnPbTe; and at least one quaternary compound selected from among SnPbSSe, SnPbSeTe, and SnPbSTe.

According to an aspect, the IV group element may be selected from among Si, Ge, and a mixture thereof. The group IV compound may be a binary compound selected from among SiC, SiGe, and a mixture thereof.

The fluorescence dye may include at least one inorganic material selected from among CdSe, CdSe/ZnS, CdTe/CdS, CdTe/CdTe, ZnSe/ZnS, ZnTe/ZnSe, PbSe, PbS InAs, InP, InGaP, InGaP/ZnS, and HgTe; and at least one organic material selected from among Cy3.5, Cy5, Cy5.5, Cy7, indocyanine green (ICG), cypate, ITCC, NIR820, NIR2, IRDye78, IRDye80, IRDye82, oxazines-based cresy violet, nile blue, oxazine 750, and rhodamines-based rhodamine800 and texas red.

According to an aspect, the tactile pad layer may form the microarray on which a plurality of structures is arranged to interlock with the plurality of structures included in the pixel layer using an elastic composite material. Due to the interlocking structure of the tactile pad layer, stress may be concentrated locally relative to a multi-directional force. Accordingly, compared to a tactile pad layer in a planar structure according to the related art, it is possible to manufacture a high resolution tactile pad layer and to sense a multi-directional tactile sense based on a difference in a contact area.

In operation 230, the pixel layer including the microarray may be provided on the total reflection layer formed using the acrylic material.

In operation 240, the tactile pad layer including the microarray in the interlocking structure with the structures of the pixel layer may be provided on the pixel layer.

A method of manufacturing a tactile sensor according to some example embodiments may provide a tactile sensor with a high sensitivity, a multi-functionality, and a multi-directionality capable of sensing various external forces by manufacturing the tactile sensor in a microarray interlocking structure.

According to an example embodiment, there is provided a 3D mapping method including acquiring a 3D image based on color information provided in response to a tactile signal sensed by the tactile sensor.

The 3D mapping method may three-dimensionally recognize an external stimulus by emitting at least one of an NIR light, a visible light, and a UV light to excite at least one color conversion mediator selected from a UCN particle, a quantum dot, and a fluorescence dye, by detecting a visible light emitted from the excited color conversion mediator, and by applying a frustrated total internal reflection (FTIR) phenomenon. The sensitivity of pressure may be adjusted and thereby transferred from the tactile pad layer to the pixel layer. A specific pattern of contact occurs on the total reflection layer based on a magnitude and a direction of the pressure transferred to the pixel layer including the microarray. The microarray in contact with the total reflection layer may emit a light in the specific pattern based on the magnitude and the direction of pressure. The emission pattern may be analyzed using a simulation-based 3D mapping scheme and used to recognize a tactile sense.

Figure 6:
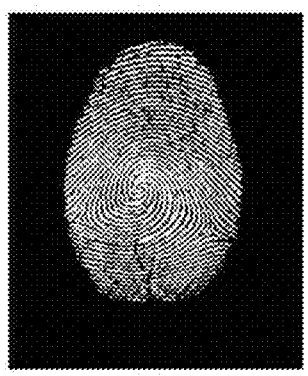
FIG. 6, images (a), (b), and (c), illustrate patterns acquired by recognizing a fingerprint using a conventional tactile sensor and a tactile sensor according to an example embodiment.
Figure 6:
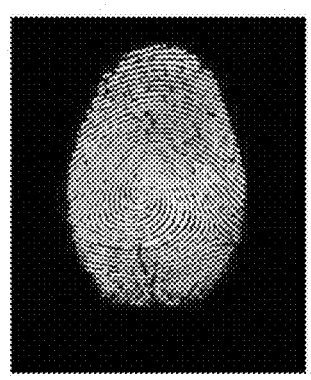
Figure 6:
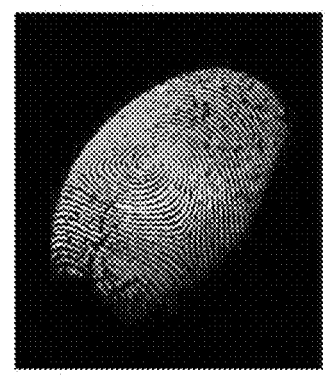

FIG. 6, images (a), (b), and (c), illustrate patterns acquired by recognizing a fingerprint using a conventional tactile sensor and a tactile sensor according to an example embodiment. The image (a) of FIG. 6 illustrates a fingerprint pattern acquired after recognizing a fingerprint using a conventional pressure-based tactile sensor, the image (b) of FIG. 6 illustrates a color fingerprint pattern acquired after recognizing a fingerprint using a tactile sensor according to an example embodiment, and the image (c) of FIG. 6 illustrates a fingerprint pattern acquired by applying a 3D mapping method to the image (b) of FIG. 6.

A 3D mapping method according to some example embodiments may be applied to a biometric security technology such as a fingerprint recognition, a medical device for rehabilitation training and physical therapy, and the like.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A tactile sensor comprising:
a total reflection layer;
a pixel layer formed on the total reflection layer and including a microarray; and
a tactile pad layer formed on the pixel layer.

2. The tactile sensor of claim 1, wherein the microarray includes at least one color includes at least one color conversion mediator selected from among a upconverting nanocrystal (UCN) particle, a quantum dot, and a fluorescence dye.

3. The tactile sensor of claim 2, wherein the UCN particle includes at least one selected from a group consisting of $(NaYF_4:Yb^{3+},Er^{3+})$, $(NaYF_4:Yb^{3+},Tm^{3+})$, $(NaGdF_4:Yb^{3+}, Er^{3+})$, $(NaYF_4:Yb^{3+},Er^{3+}/NaGdF_4)$, and $(NaGdF_4:Yb^{3+}, Er^{3+}/NaGdF_4)$.

4. The tactile sensor of claim 2, wherein the quantum dot includes at least one selected from a group consisting of a group II-VI compound, a group III-V compound, a group IV-VI compound, a group IV element, and a group IV compound.

5. The tactile sensor of claim 2, wherein the fluorescence dye includes
at least one inorganic material selected from a group consisting of CdSe, CdSe/ZnS, CdTe/CdS, CdTe/CdTe, ZnSe/ZnS, ZnTe/ZnSe, PbSe, PbS InAs, InP, InGaP, InGaP/ZnS, and HgTe; and
at least one organic material selected from a group consisting of Cy3.5, Cy5, Cy5.5, Cy7, indocyanine green (ICG), cypate, ITCC, NIR820, NIR2, IRDye78, IRDye80, IRDye82, oxazines-based cresy violet, nile blue, oxazine 750, and rhodamines-based rhodamine800 and texas red.

6. The tactile sensor of claim 1, wherein at least one light selected from among near infrared (NIR) light, visible light, and ultraviolet (UV) light is irradiated toward the total reflection layer.

7. The tactile sensor of claim 1, wherein the microarray is configured by arranging a plurality of structures at predetermined intervals.

8. The tactile sensor of claim 7, wherein each of the plurality of structures is provided in a shape of at least one of a dome, a cylinder, a cone, a ridge, a faceted cone, a faceted cylinder, a faceted semi-sphere, and a faceted sphere.

9. The tactile sensor of claim 7, wherein each of the plurality of structures has a diameter of 10 μm to 100 μm and a height of 5 μm to 50 μm.

10. The tactile sensor of claim 7, wherein the microarray includes the plurality of structures each having a different height and a different shape per single pixel.

11. The tactile sensor of claim 1, further comprising:
a spacer layer provided between the total reflection layer and the pixel layer.

12. The tactile sensor of claim 11, wherein a refractive index of the total reflection layer is greater than that of the spacer layer.

13. A method of manufacturing a tactile sensor, the method comprising:
preparing a total reflection layer using an acrylic material;
forming a pixel layer that includes a microarray on which a plurality of structures is arranged at predetermined intervals and a tactile pad layer that includes a microarray on which a plurality of structures is arranged to interlock with the plurality of structures included in the pixel layer;
providing the pixel layer on the total reflection layer; and
providing the tactile pad layer on the pixel layer.

14. The method of claim 13, wherein the preparing of the total reflection layer comprises preparing the total reflection layer by replacing the acrylic material with halogen and by adding a metal oxide nanoparticle to the acrylic material replaced with the halogen.

15. The method of claim 13, further comprising
preparing a porous spacer layer after the preparing of the total reflection layer.

16. The method of claim 13, wherein the pixel layer forms the microarray including the plurality of structures using a three-dimensional (3D) optical etching method after dispersing at least one color conversion mediator selected from among an upconverting nano crystal (UCN) particle, a quantum dot, and a fluorescence dye to flexible resin.

17. The method of claim 13, wherein the tactile pad layer forms the microarray on which the plurality of structures is arranged to interlock with the plurality of structures included in the pixel layer using an elastic composite material.

18. A three-dimensional (3D) mapping method comprising acquiring a 3D image based on color information provided in response to a tactile signal sensed by the tactile sensor of claim 1.

* * * * *